United States Patent
Hanebaum et al.

[11] Patent Number: 5,927,973
[45] Date of Patent: Jul. 27, 1999

[54] APPARATUS AND METHOD FOR MEASURING THE POSITION OF THE OCCLUSAL PLANE OF THE MOUTH

[76] Inventors: Allen Hanebaum, 10105 Donegal Ct.; Herbert L. Robinson, 10104 Newhall Rd., both of Potomac, Md. 20854

[21] Appl. No.: 08/988,213

[22] Filed: Dec. 10, 1997

[51] Int. Cl.$^6$ ............................................. A61C 19/04
[52] U.S. Cl. ........................ 433/72; 600/590; 33/513
[58] Field of Search ................ 433/72, 73; 600/590; 33/513, 514

[56] References Cited

U.S. PATENT DOCUMENTS

| | | |
|---|---|---|
| 1,188,416 | 6/1916 | Dalbey . |
| 1,525,305 | 2/1925 | Leary . |
| 1,662,670 | 3/1928 | Harter ........................................ 433/73 |
| 1,804,567 | 5/1931 | Pray ........................................... 433/72 |
| 1,976,045 | 1/1934 | Sorenson . |
| 2,656,603 | 10/1953 | Brassie . |
| 3,084,438 | 4/1963 | Goodfriend . |
| 3,200,497 | 8/1965 | Goodfriend . |
| 4,411,622 | 10/1983 | Hansen . |
| 4,575,805 | 3/1986 | Moermann et al. . |
| 4,611,288 | 9/1986 | Duret et al. . |
| 4,634,377 | 1/1987 | Behrend . |
| 4,663,720 | 5/1987 | Duret et al. . |
| 4,687,003 | 8/1987 | Burckhardt . |
| 4,843,720 | 7/1989 | Kim ........................................... 433/72 |
| 4,859,181 | 8/1989 | Neumeyer ............................... 600/590 |
| 4,935,635 | 6/1990 | O'Harra . |
| 4,996,994 | 3/1991 | Steinhauer et al. . |
| 5,030,956 | 7/1991 | Murphy . |
| 5,143,086 | 9/1992 | Duret et al. ............................... 433/69 |
| 5,176,515 | 1/1993 | Andrews .................................. 433/24 |
| 5,227,797 | 7/1993 | Murphy .................................... 342/22 |
| 5,244,387 | 9/1993 | Fuierer ...................................... 433/72 |
| 5,278,756 | 1/1994 | Lenchen et al. . |
| 5,440,393 | 8/1995 | Wenz ........................................ 356/376 |
| 5,588,430 | 12/1996 | Bova et al. ................................ 433/68 |
| 5,598,269 | 1/1997 | Kitaevich et al. . |

*Primary Examiner*—Ralph A. Lewis
*Attorney, Agent, or Firm*—Hoffman, Wasson & Gitler

[57] ABSTRACT

An instrument and method to measure the position of the occlusal plane of the mouth with reference to the structural features of the cranium. The instrument includes a vertical face bow, positioned on the nasal bridge and the forward edge of the base of the chin. The device employs light beams to make measurements of the patient's occlusal plane and the nose-to-chin distances. The device utilizes an internal processor to make the necessary calculations, provides direct numerical readouts, is battery powered and self-calibrating. The entire device is sealed to permit cold sterilization by liquids.

19 Claims, 5 Drawing Sheets

APPARATUS AND METHOD FOR MEASURING THE POSITION OF THE OCCLUSAL PLANE OF THE MOUTH

FIELD OF THE INVENTION

The present invention pertains to an instrument and method to measure the position of the occlusal plane of the mouth with reference to the structural features, i.e., the bones, of the cranium. More particularly, the occlusal plane is the "bite plane," the surface where the upper and lower sets of teeth meet. The determination of its location is essential in the creation of satisfactory dental prostheses such as upper and lower dentures or major bridges.

The device of the present invention measures the position of the front edge of the occlusal plane with respect to both the nasal bridge and the base of the chin of the patient.

BACKGROUND OF THE INVENTION

The need for reconstructive surgery of teeth by means of full or partial upper and/or lower dentures is common, particularly among older people and those who have suffered an injury.

The reconstructive process typically begins by the dentist taking impression molds of the patient's remaining teeth and gums. These impressions are made by having the patient bite into soft impression material held in a U-shaped tray that fits around the teeth and gums. These negative molds, when hardened, are then used to make models by casting, in wax and/or plaster or similar plastic materials, of the tooth and gum structure. These positive models are then mounted in a device called an articulator, by a technician who then makes preliminary adjustments for bite interface, fit and appearance. The technician sends the models to the dentist, who proceeds to make further adjustments while fitting the models to the patient. the adjusted models are then used as the basis for the final prothesis.

A major drawback in the foregoing procedure is relating the initial models, taken by the dentist, to positions of the models in the articulator, so the technician can adjust the models for the correct mouth fit. It should be noted that even if the prosthesis fits well over the gums, improper mouth fit, caused by either improper tooth position or an incorrect relationship between the upper and lower teeth is a major source of patient discomfort. Rework is costly, time consuming and often produces even more patient complaints.

Proper, accurate measurement of the occlusal plane will greatly reduce the foregoing problems. It will also simplify the process of checking fit during the intermediate stages when working with the preliminary molds in the patient's mouth, prior to creating the final prosthesis.

Three methods have been most frequently used to reduce the problems mentioned above. The first is by the use of instruments called "face bows." A second method is by the use of instruments that trace the "gothic arch" of lower jaw motion. The third method has been to use no instruments at all, but rather for a dentist to "eyeball" the measurements and trust to luck and a skilled technician at the articulator.

A face bow, as the name implies, is a bow-shaped metallic device whose ends are referenced to some feature of the human skull. Nearly all face bows are oriented horizontally and the ends are referenced to the ear holes. For example, U.S. Pat. Nos. 3,084,438 and 3,200,497 (Goodfriend) relate to horizontal bows which rest in the ears, using plugs, and on the bridge of the nose. U.S. Pat. No. 1,188,416 (Dalbey) pertains to a device for measuring the occlusal plane. The device is a horizontal face bow, connected to the ear holes and resting on the bridge of the nose and under the nose.

A few face bows are referenced to the temporal-mandibular-joint (TMJ), but such referencing is very difficult, and therefor such face bows are rarely employed. For example, U.S. Pat. No. 4,411,622 (Hansen) discloses a device for locating the jaw hinge (TMJ) rather than using the ear holes for a bow reference. Typically, the ends of the horizontal bow have tapered plugs which are inserted into the ears. A third reference point is needed to establish a reference plane to measure from, and the bridge of the nose is often used as such a reference point. Occasionally the third reference point is the forehead or just a level indicator. See for example, U.S. Pat. No. 5,176,515 (Andrews) which illustrates a dental treatment method and apparatus.

The flaw in the foregoing method is that the human face is not symmetrical and ear holes are "soft" mountings with respect to the bone structure. As a result, the bow will usually be tilted and off center. Furthermore, when reset for a later measurement, the new setting will most likely not be in the same plane due to the soft mounting. To summarize, the measurements are not closely repeatable and are not very accurate.

Since the foregoing bows are all entirely mechanical in adjustment and in setting, they are awkward, slow, and often hard to read as the fiducial markings must be poorly placed. The measurements are made by attaching a probe to the bow and then moving it in height and inward toward the teeth. The probe must just touch the edge of the teeth (or tooth) or the gums where there are no existing teeth. Such positioning requires some delicacy and skill and the patient must remain as motionless as possibly for a significant period of time. In addition, horizontal face bows make no measurements with reference to the lower jaw, which leaves out important data for the articulator technician.

Vertical face bows are rare, and the present inventors are only aware of one patent to Sorenson, U.S. Pat. No. 1,976,045. Such a vertical face bow eliminates some of the drawbacks inherent in the use of horizontal bows. In particular, the vertical face bow is centered, it rests against firm cranial features, namely the nasal bridge and chin, and has a lower jaw reference. A vertical face bow is also potentially more repeatable. However, a vertical face bow requires more skill on the part of the dentist to take advantage of its design.

Some instruments establish the bite plane by means of tracing the movement of the teeth horizontally. An example is U.S. Pat. No. 2,656,603 to Brassie which relates to an instrument for relating casts to dental articulators and traces the horizontal movements of the lower jaw to measure aspects of the occlusal plane. A frame is fastened to the head and a flat plate is attached and inserted into the mouth. The lower Jaw is moved in a horizontal fashion. The teeth trace out a pattern resembling a gothic arch on a sheet of paper attached to the plate. While this pattern establishes the entire bite plane, rather than just the front edge, the method suffers from all the drawbacks of a horizontal face bow plus it is more awkward to use and to reference. It is seldom used except for the different function of bite or jaw analysis.

Oddly enough, many dentists take no occlusal plane measurements at all. They rely on the skills of the technician working with the articulator, plus their own skills during multiple fittings. Usually, they arrive at a good result; despite the fact that this takes considerable time of both the dentist, his or her staff, the technician, and not least the patient. Of course, this drives up the cost and exposes all to the risk of error. Major errors, and consequent rework, may necessitate scrapping the initial prosthesis and starting again.

The reason that this method is so often used is that the other methods work so poorly, for the reasons stated previously. The truth is that no measurements, or rather the visual techniques of the dentist and technicians are rarely worse than using the available instruments.

The instruments can produce useful data in the hands of a highly skilled dentist, but this is just the person who can estimate values well without instruments.

What is required is an instrument that is easy to use, quick, accurate, and can take repeatable measurements that are of value to both dentist and technician. The proposed invention is such an instrument.

SUMMARY OF THE INVENTION

The present invention is designed to overcome the drawbacks of previous methods and offers additional advantages.

An object of the present invention is to permit easy operation with rapid taking of measurements to reduce patient inconvenience.

Another object the present invention is to provide an instrument which produces repeatable measurements; i.e., produces the same values each time a measurement of the same object is taken.

Yet another object of the present invention is to improve the accuracy of the measurements above that of present methods.

Still another object of the present invention is to provide an instrument which takes measurements that permit referencing to both the upper and lower jaw.

Another object of the present invention is to provide an instrument which takes measurements while avoiding contact with the patient's mouth, teeth, or gums. This reduces patient discomfort and permits easy sterilization.

Yet another object of the present invention is to provide an instrument which can be produced at low cost.

To achieve the foregoing and other objects, the present invention is directed to a vertical face bow, positioned on the nasal bridge and the forward edge of the base of the chin. The device employs light beams to make measurements of the patient's occlusal plane and the nose-to-chin distances. The device utilizes an internal processor to make the necessary calculations, provides direct numerical readouts, is battery powered and self-calibrating. The entire device is sealed to permit cold sterilization by liquids.

BRIEF DESCRIPTION OF THE DRAWINGS

The foregoing and other objects and attributes of the present invention will be described with respect to the following drawings in which.

DETAILED DESCRIPTION OF THE PREFERRED EMBODIMENTS

Figure 1:
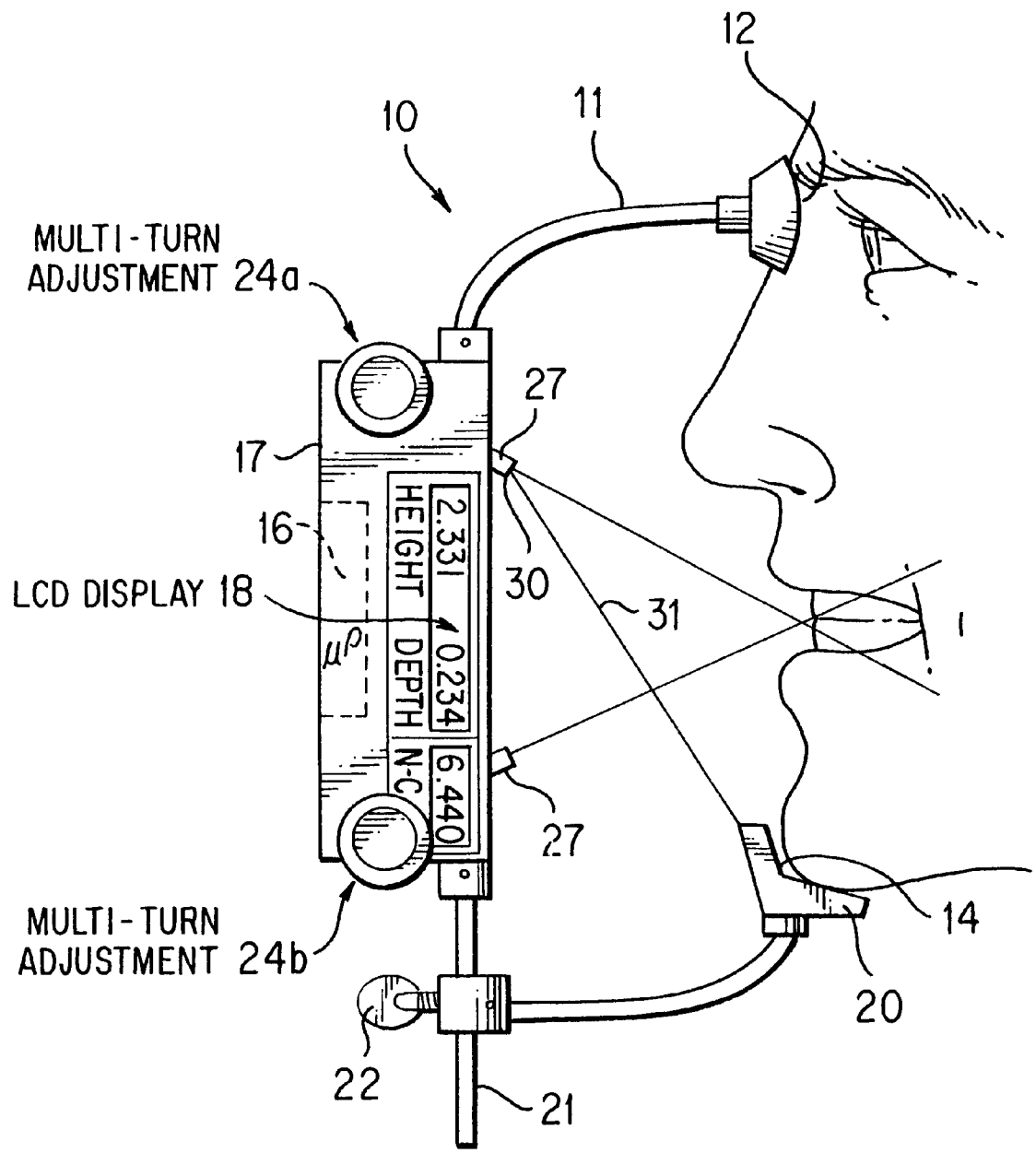
FIG. 1 is a side view of a first embodiment of the present invention.

The present invention is directed to a dental occlusal instrument 10 in the form of a vertical face bow 11. It is hand-held by the dentist and measurements from it are referenced to the bridge 12 of the nose and the front of the base of the chin 14 of the patient.

A major point of novelty in the present invention is that the measurements are taken using light beams, so that there is no contact made with the patient's mouth. The process of taking the measurements is rapid, clean and accurate.

The measurements are calculated, using basic trigonometry, by an internal microprocessor 16 contained in a housing 17. The calculating is performed automatically, and the results are displayed on a display or numerical indicator 18. The apparatus is simple to operate requiring no specialized skill and the dentist needs to make only two adjustments.

Figure 2:
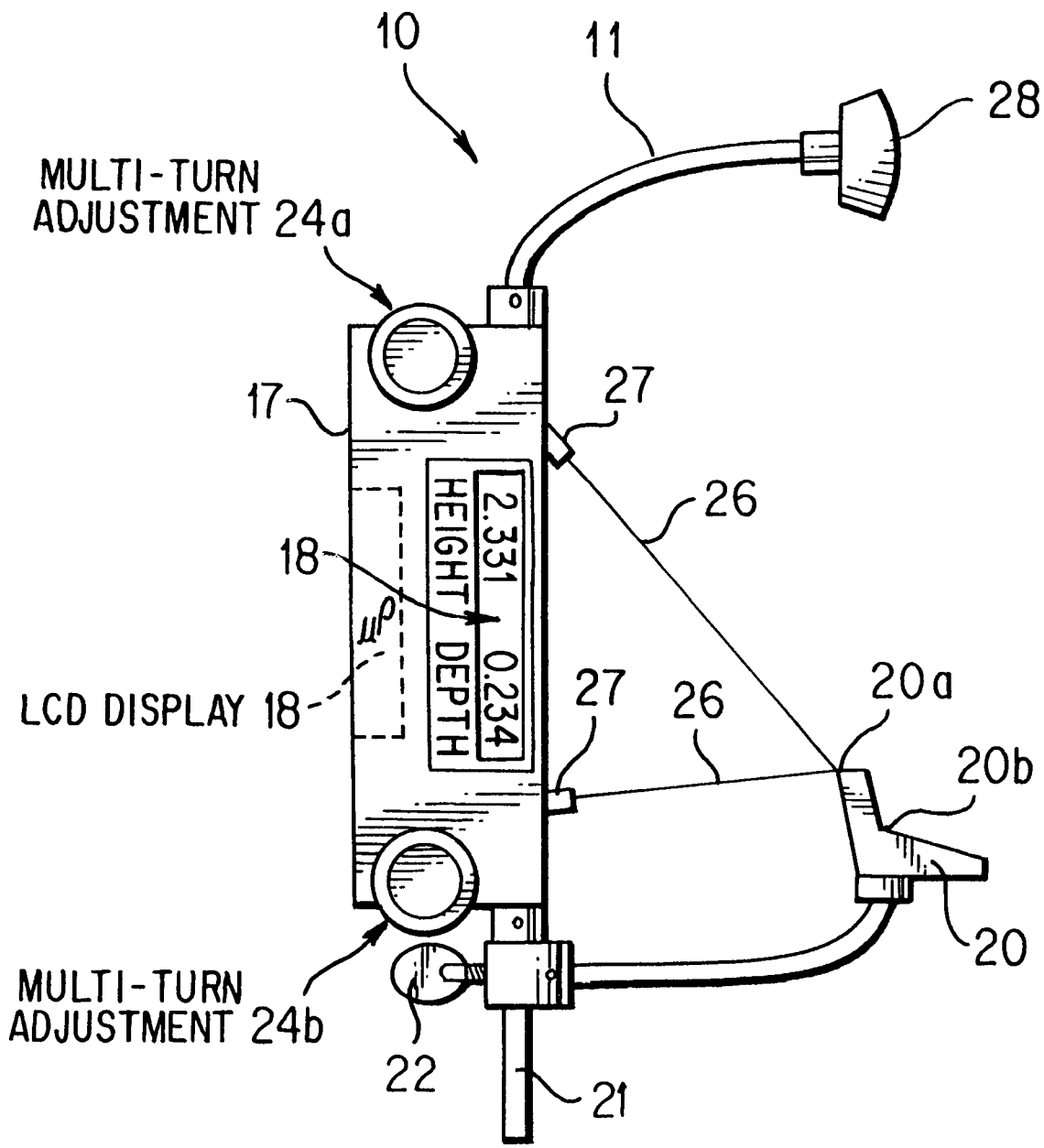
FIG. 2 is a side view of a second embodiment of the present invention.

In practice, prior to use, the dentist moves the chin rest 20 along a support pole 21, which extends up to said housing 17, to its highest or maximum vertical position, as shown in FIG. 2, and tightens the locking screw 22. The dentist then rotates the two multi-turn adjustment knobs 24a and 24b so that the light beams 26 intersect at the front edge 20a of the chin rest 20 as shown in FIG. 2. The display 18 will then read the predetermined values for such a setting, thereby calibrating the instrument 10, which is another novel feature of the present invention. If the readout is incorrect, indicating that the apparatus 10 is out of calibration, the values can be reset. The instrument 10 is now ready for use.

The dentist now slides the chin rest 20 downward. The patient is directed to approach the apparatus while keeping his or her jaws closed, and to draw back his or her lips from his or her teeth.

The upper rest 28 is then set upon the patients nasal bridge 12 by the dentist, along the center line of his or her face. The chin rest 20 is then moved under the patient's chin, at the forward edge, so that the chin 14 rests in the notch 20b of the chin rest 20 as shown in FIG. 1, and the rest is locked in place by the locking screw 22.

The dentist next rotates the multi-turn adjustment knobs 24a and 24b to aim the light beams 26, from light source 27, so that they intersect on the feature to be measured (tooth edge or gum for example). The light beams 26 are shown as lines 1 in FIG. 1.

The instrument 10 then automatically calculates the height and depth of the point to be measured, referenced to the bow 11, and the nasal bridge 12.

To measure the bridge-to-chin distance, the dentist adjusts the upper beam 26a, by means of the adjacent knob 24a, to aim at the edge of the chin rest 20, shown by line 2 in FIG. 1. Since the mechanical design fixes the depth, only one beam is needed to measure the position of the chin rest 20. This measurement can be taken with the bow 11 removed from the patient's face.

Figure 3:
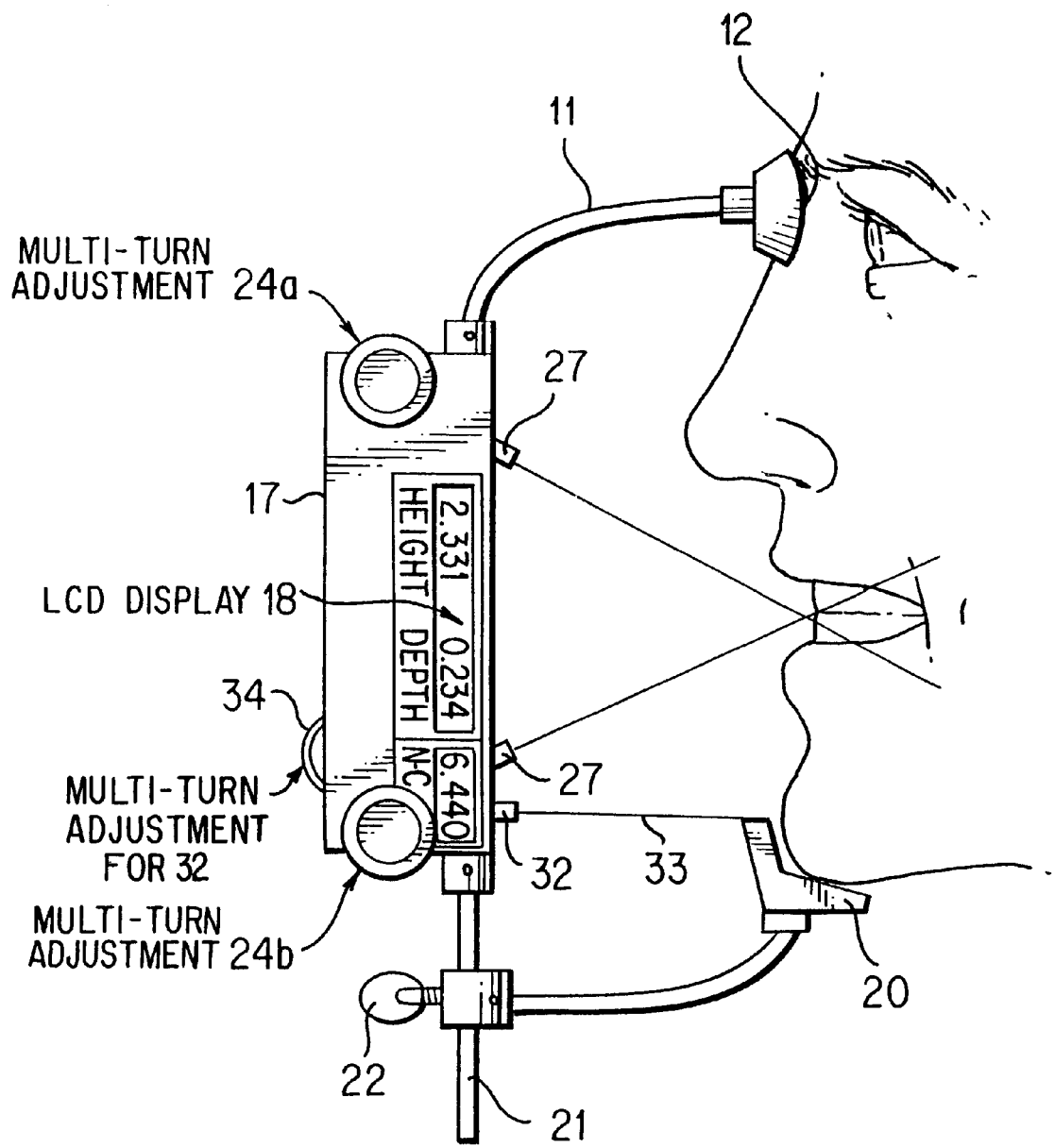
FIG. 3 is a side view of the second embodiment shown in FIG. 2 having a third light source.

In the embodiment shown in FIG. 3, a third light source 32 is provided near the lower light source, and produces a light beam 33 to measure the position of the chin rest 20. The third light source 32 is adjusted by multiturn adjustment knob 34.

The light sources 27 and/or 32 can be of different colors to differentiate the beams for ease of adjustment.

The device 10 will display three measurements, height, depth, and chin rest position, on the display 18 as numbers in tenths of millimeters. Prior art strives to achieve accuracy of plus or minus one millimeter (and rarely achieves it). The device 10 of the present invention achieves an accuracy of one or two tenths of a millimeter.

The light sources 27, display 18, and microprocessor 16 are housed in the housing 17, and the adjustment knobs 24 project from the housing 17.

The preferred light source is a solid state laser. The single frequency of emission of such lasers reduces diffraction. However, alternative sources can be used. For example, light emitting diodes (LEDs), miniature incandescent lamps, etc. Furthermore, the beams can be sharpened by using elements such as masks, lenses, etc. in the light paths.

The readout display 18 preferably employs liquid crystal displays, however, as alternatives, LEDs, plasmas, etc. can be used.

The multi-turn adjustment knobs 24 are potentiometers. The angular readouts to the microprocessor 16 can be, but are not limited to, resistance values, voltages, or direct coders, such as wheels.

Figure 4:
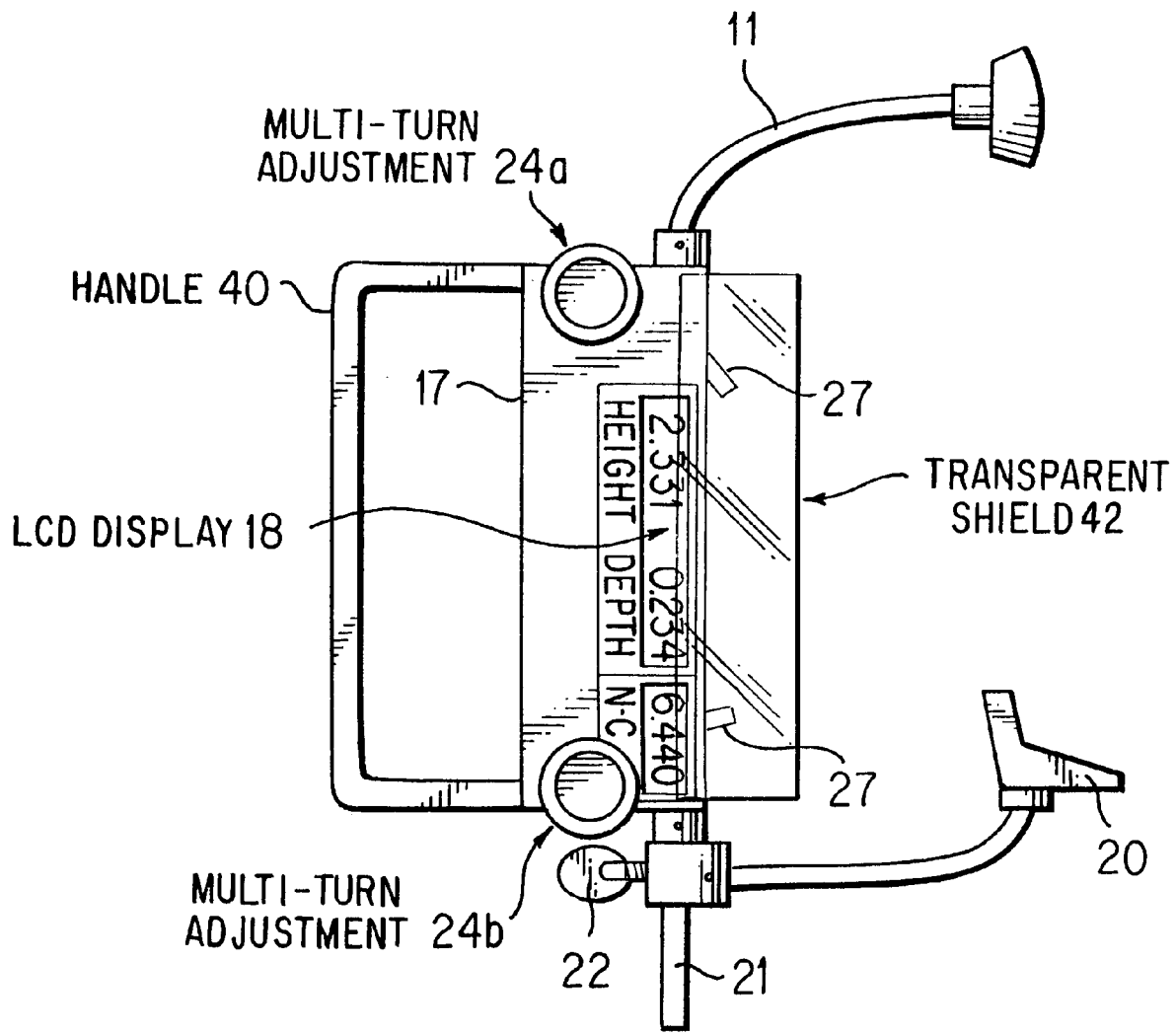
FIG. 4 is a side view of the second embodiment of FIG. 2 of the present invention having a handle and a transparent shield.
Figure 5:
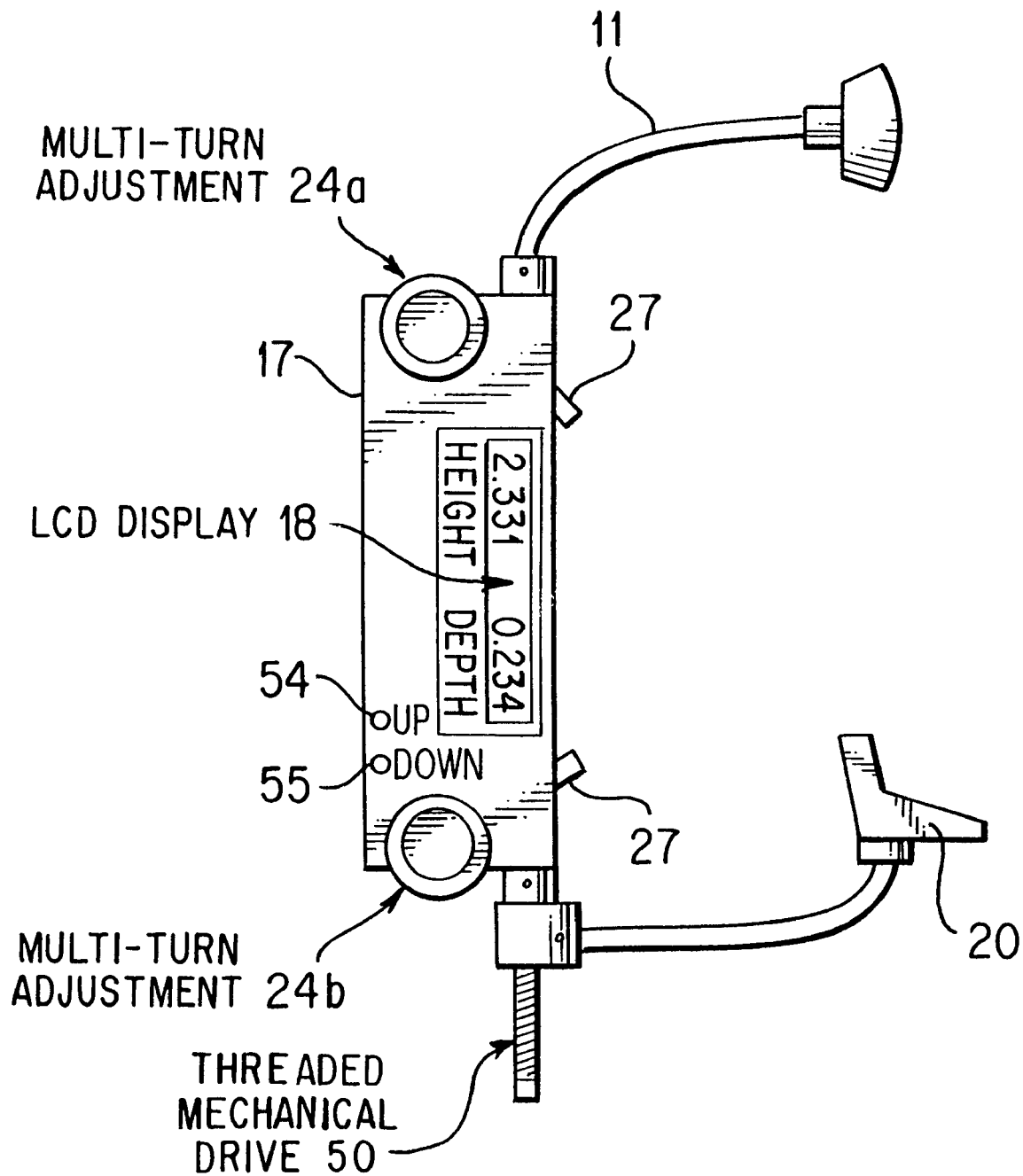
FIG. 5 is a side view of the first embodiment, shown in FIG. 1, having a mechanical drive for raising and lowering the chin rest.

Furthermore, the device 10 can be modified by adding other physical elements, such as, as shown in FIG. 4: a handle 40 for easy transport; and/or a transparent shield 42 to snap over the beam side of the device, thereby aiding in sterilization; and, as shown in FIG. 5, a mechanical or electromechanical drive 50 to move the chin rest up or down. Drive control buttons 54 and 55 are provided to move the chin rest 20 up and down, respectively.

The microprocessor 16 can be modified to have a memory storage capacity with recall provisions. A plug for a printer, as well as a built-in miniature printer, can be added to allow for the production of a hard copy of the readout values. From the foregoing, the device of the present invention is convenient for the patient and the dentist, rapid, accurate, repeatable, non-contacting to the mouth, self-calibrating and sterilizable. The device stores results and displays them, and is easy to operate and to interpret. The device produces measurements that relate to both the upper and lower jaws, which simplifies the work of the articulator technician. As a consequence, the chance for errors and/or the need for rework is greatly reduced. Further, the device can be manufactured at relatively low cost.

Having described the preferred embodiments of the present invention, it is believed that other modifications, variations and changes will be suggested to those skilled in the art in view of the description set forth above. It is therefore to be understood that all such variations, modifications and changes are believed to fall within the size of the present invention as defined in the appended claims.

What is claimed is:

1. An apparatus for measuring the position of the occlusal plane of the mouth comprising:

a vertical bow;

an upper rest, disposed at a top of said vertical bow, for positioning against a nasal bridge of a patient;

a chin rest, disposed at a bottom of said vertical bow, for positioning against a chin of said patient;

at least two light sources for projecting light beams at a feature of said patient to be measured, said at least two light sources being provided on said vertical bow between said upper rest and said chin rest;

means for adjusting said at least two light beams;

a microprocessor for calculating a height and depth of said feature relative to said vertical bow, said microprocessor performing said calculations of said height and depth based upon said at least two light beams after adjustment by said adjusting means; and display means receiving an output from said microprocessor, for displaying said height and depth measurements.

2. An apparatus as recited in claim 1, wherein said at least two light sources are laser beams.

3. An apparatus as recited in claim 1, wherein said adjusting means are knobs which control angular orientation of said at least two light sources.

4. An apparatus as recited in claim 1, further comprising means for adjusting a height of said chin rest relative to said at least two light sources and said upper rest.

5. An apparatus as recited in claim 4, wherein said adjusting means is a mechanical drive.

6. An apparatus as recited in claim 5, wherein said bridge to chin distance measurement is calculated by said microprocessor by adjusting one of said at least two light sources to intersect a front edge of said chin rest.

7. An apparatus as recited in claim 4, wherein said microprocessor calculates said height and said depth when said light sources are adjusted to intersect at said feature to be measured.

8. An apparatus as recited in claim 1, wherein said display means is a liquid crystal display.

9. An apparatus as recited in claim 1, wherein said at least two light sources, said display and said microprocessor are contained in a housing near a center of said vertical bow.

10. A method of measuring the position of the occlusal plane of the mouth using a dental occlusal instrument comprising the steps of:

positioning a vertical bow in front of a patient's face;

positioning an upper rest, disposed at a top of said vertical bow, against a nasal bridge of said patient;

positioning a chin rest, disposed at a bottom of said vertical bow, against a chin of said patient;

projecting at least two light beams from at least two separate light sources near a center of said face bow at a feature of said patient to be measured;

adjusting said at least two light beams;

calculating a height and depth of said feature relative to said vertical bow utilizing said at least two light beams after said adjusting step; and displaying said height and depth measurements produced from said calculating step.

11. A method as recited in claim 10, wherein said at least two light sources are laser beams.

12. A method as recited in claim 10, wherein said adjusting means control angular orientation of said at least two light sources.

13. A method as recited in claim 10, comprising the further step of adjusting a height of said chin rest relative to said at least two light sources and said upper rest.

14. A method as recited in claim 13, wherein said calculating step is performed when said light sources are adjusted to intersect at said feature to be measured.

15. A method as recited in claim 10, comprising the further step of displaying a bridge-to-chin distance measurement produced by said microprocessor.

16. A method as recited in claim 15, wherein said step of calculating said bridge to chin distance measurement is performed when said at least two light sources are adjusted to intersect a front edge of said chin rest.

17. A method as recited in claim 11, wherein said display means is a liquid crystal display.

18. A method as recited in claim 10, wherein said feature to be measured is one of a tooth edge and gum.

19. A method as recited in claim 10, wherein prior to said positioning step said chin rest is positioned at a maximum vertical position, said at least two light beams are adjusted to intersect a front edge of said chin rest, and calculated measurements to said chin rest are compared with predetermined values to calibrate said dental occlusal instrument.

* * * * *